United States Patent

Su et al.

[11] Patent Number: 6,060,625
[45] Date of Patent: May 9, 2000

[54] PROCESS FOR THE PRODUCTION OF ETHERAMINE ALKOXYLATES

[75] Inventors: Wei-Yang Su, Austin; Mike W. McKinney, Cedar Park; Timothy L. Lambert; Edward T. Marquis, both of Austin, all of Tex.

[73] Assignee: Huntsman Petrochemical Corporation, Austin, Tex.

[21] Appl. No.: 09/303,170

[22] Filed: Apr. 30, 1999

[51] Int. Cl.[7] .................................................. C07C 211/03
[52] U.S. Cl. .......................... 564/505; 564/399; 564/424; 564/475; 564/504
[58] Field of Search ................................... 564/505, 399, 564/424, 475, 504

[56] References Cited

U.S. PATENT DOCUMENTS

| | | | |
|---|---|---|---|
| 3,654,370 | 4/1972 | Yeakey | 260/584 |
| 4,391,610 | 7/1983 | Vipond et al. | |
| 5,352,835 | 10/1994 | Dai, et al. | 564/480 |
| 5,616,811 | 4/1997 | Sung et al. | |

OTHER PUBLICATIONS

Patent Specification for 1588079 Filed May 24, 1978.

*Primary Examiner*—Samuel Barts
*Attorney, Agent, or Firm*—O'Keefe, Egan & Peterman

[57] ABSTRACT

A process for the alkoxylation of a polyetheramine to form an etheramine alkoxylate. In the process, a polyetheramine is reacted with an alkylene oxide in the presence of an alcohol to form the etheramine alkoxylate. The alcohol serves as a catalyst to allow the reaction proceed at a heightened temperature as compared to the reaction in the absence of alcohol, while at the same time limiting the amount of glycol by-product production which would otherwise typically form when higher polyetheramines are to be alkoxylated. The alcohol may be, for instance, ethanol or methanol.

20 Claims, No Drawings

PROCESS FOR THE PRODUCTION OF ETHERAMINE ALKOXYLATES

BACKGROUND OF INVENTION

This invention concerns a process for the production of an etheramine alkoxylate that may be used in a fuel composition containing a petroleum fuel.

Petroleum distillates have long been used as fuels for internal combustion engines. In recent years, research has been directed toward preparing fuel compositions containing additive which acts as a surface-active agent for improving fuel distribution to prevent poor driving performance due to the maldistribution of fuel-air mixture between the cylinders. Etheramine alkoxylates have been found utility in such fuel compositions. Owing to the interest in these compounds, improved methods of production are desirable.

The inventors herein recognized that higher amines were difficult to alkoxylate. Typically, water has been used to catalyze the reaction. It has been found that the reaction is still somewhat slow under the normal operation temperature, despite use of water as the reaction catalyst. If the temperature is raised to force the reaction to proceed faster, however, the corresponding glycol, an unwanted by-product, would be produced in a significant quantity. A faster reaction that does not produce large quantities of unwanted by-product glycols would be highly desirable.

SUMMARY OF INVENTION

This invention is a novel process for the production of etheramine alkoxylates, which provides a solution to one or more of the problems, needs and disadvantages described above.

In one broad respect, this invention is a process for the production of an etheramine alkoxylate, comprising: reacting a polyetheramine with an alkylene oxide in the presence of an alcohol under conditions effective to form the etheramine alkoxylate.

In another broad respect, this invention is a process for the production of an etheramine alkoxylate, comprising: reacting a polyetheramine with an alkylene oxide in the presence of an alcohol to form the etheramine alkoxylate, wherein the alcohol is methanol, ethanol, propanol or a mixture thereof; wherein the alkylene oxide is ethylene oxide, propylene oxide, a butylene oxide or a mixture thereof; wherein the polyetheramine is of formula: R—(OCH$_2$CHR$^1$)$_m$—NH$_2$ wherein R is a straight or branched alkyl, an alicyclic, an alkylalicyclic radical having from 1 to 30 carbon atoms or R$^2$—Ar—; R$^1$ is independently in each occurrence hydrogen or alkyl from 1 to 6 carbons; R$^2$ is independently in each a hydrocarbyl radical having 1 to 18 carbon atoms; m is from 2 to 20.

The process of this invention provides shorter reaction time for production of etheramine alkoxylates than presently available by other processes. Also, the process of this invention produces etheramine alkoxylate having less by-product as compared to other processes which do not use alcohol and run at higher temperatures. Thus, advantageously, this process may be run at elevated temperatures relative to conventional processes so that higher etheramine alkoxylates may be produced. The etheramine alkoxylates made by the process of this invention are useful as additives for fuel compositions for internal combustion engines and the like.

DETAILED DESCRIPTION OF THE INVENTION

The starting materials for preparing the etheramine alkyloxylates of this invention may be an alkoxylated alcohol or alkoxylated phenol of the formula, R—(OCH$_2$CHR$^1$)$_m$—OH, wherein R is a straight or branched alkyl, an alicyclic, an alkylalicyclic radical having from 1 to 30 carbon atoms or R$^2$—Ar—; R$^1$ is independently in each occurrence hydrogen or a straight chain or branched alkyl from 1 to 6 carbons; R$^2$ may be independently in each occurrence a hydrocarbyl radical of from 1 to 18 carbon atoms; and wherein m may vary from 2 to 20, with m preferably being from about 5 to about 20. Representative, non-limiting examples of such straight or branched alkyl groups include methyl, ethyl, n-propyl, iso-propyl, n-butyl, sec-butyl, iso-butyl, t-butyl and higher alkyls. When R$^1$ or R$^3$ is alkyl, it is preferred that the alkyl be methyl, ethyl, n-propyl or iso-propyl. Representative, non-limiting examples of Ar include divalent arylene moieties having from about 6 to about 24 carbon atoms such as moieties derived from benzene, naphthalene and anthracene, particularly benzene. Representative, non-limiting examples of suitable hydrocarbyl groups for R$^2$ include methyl, ethyl, propyl, butyl, pentyl, hextyl, heptyl, octyl, nonyl and higher alkyls. The alkoxylated alcohol or alkoxylated phenol starting materials may be prepared by known methods, such as by alkoxylation of alcohols and phenols with alkylene oxide in the presence of an alkoxylation catalyst such as NaOH or KOH.

The alkoxylated alcohol or phenol is reacted with ammonia using known techniques, such as by reaction with ammonia in the presence of an amination catalyst to produce a polyetheramine. The amination step typically is conducted at a temperature in the range from about 100 to about 300 degrees Centigrade, preferably from about 190 to about 220 degrees Centigrade. The pressure is typically maintained in the range from about 500 to about 5000 psi. One such amination procedure is described in U.S. Pat. No. 5,616,811. The polyetheramine may be of formula: R—(OCH$_2$CHR$^1$)$_m$—NH$_2$ wherein R, m R$^1$ are as defined above.

The polyetheramine is next alkoxylated with an alkylene oxide to produce etheramine alkoxylates. The general alkoxylation reaction known and is described, for example, in U.S. Pat. No. 4,391,610, the contents of which are incorporated herein by reference. The amounts of alkylene oxide and polyetheramine are selected to afford etheramine alkoxylates, particularly of formula:

$$R—(OCH_2CHR^1)_m—N—(H)_p(CH_2CHR^3OH)_q$$

where R and m are as described above and wherein R$^3$ is independently in each occurrence hydrogen or a straight chain or branched alkyl from 1 to 6 carbons, and wherein p+q equals 2. It should be appreciated that in a given reaction product, a mixture of mono- and di-alkoxylates may be present; hence, the values for p and q may not be whole numbers with respect to the mixture. It should also be appreciated that for individual product constituents, p may be 0 or 1 and q may be 1 or 2. In general, this reaction is conducted by contacting a polyetheramine with an alkylene oxide in the presence of an alcohol under conditions effective to form the etheramine alkoxylate. Representative, non-limiting examples of such alkylene oxides include ethylene oxide, propylene oxide, butylene oxide or mixtures thereof. This process may be run batch-wise or continuously. Depending on starting materials, the reaction conditions may be, in general, a temperature in the range from about 100 degrees Centigrade to about 250 degrees Centigrade and a positive (super-atmospheric) pressure. In one embodiment of this invention, the temperature is maintained in the range from about 125 degrees Centigrade to about 200 degrees Centigrade.

The alcohols that may be used in the practice of this invention during the alkoxylation reaction include alcohol that serve to catalyze the alkoxylation reaction. In one embodiment of this invention, the alcohol may be an aliphatic alcohol that contains from 1 to 12 carbons. Representative, non-limiting examples of such alcohols include alkanols such as methanol, ethanol and propanol as well as polyols including dihydric alcohols such as ethylene glycol and propylene glycol. The alcohol is employed in an amount effective to allow the alkoxylation to proceed at a higher temperature, which results in a shorter reaction time. The amount used may vary depending on the type of starting materials and alcohol, temperature, pressure and the like. In general during the practice of this invention, the amount of alcohol may be used in an amount such that the mole ratio of the alcohol to the polyetheramine is greater than about 1:1. In certain embodiments, the mole ratio is greater than about 1.2:1, greater than about 2:1. In general, the mole ratio is less than about 10:1, and in certain embodiments is less than about 3:1.

The etheramine alkoxylates made by the process of this invention may be used to form fuel compositions. Representative examples of suitable fuels include petroleum distillate fuels such, but not limited to, gasoline, diesel and the like. The concentration of etheramine alkoxylate may vary depending on a wide variety of factors such as presence of detergents, dispersants, and other additives; and the like. Generally, the etheramine alkoxylate is present in an amount effective to provide fuel distribution properties of the composition. For example, the etheramine alkoxylate may be employed in a concentration of from about 10 parts per million to about 5000 parts per million. The etheramine alkoxylate may be formulated as a concentrate, using a petroleum distillate as the base stock. In gasoline fuels, other fuel additives may also be included such as antiknock agents such as methylcyclopentadienyl manganese tricarbonyl, tetramethyl, or tetraethyl lead, or other dispersants or detergents such as various substituted succinimides, amines, etc. The fuel compositions may be readily prepared by, for example, dispersing an etheramine alkoxylate in a selected petroleum distillate fuel as by adding the etheramine alkoxylate to a petroleum distillate and stirring or otherwise agitating the resulting solution to evenly disperse the etheramine alkoxylate in the composition. In this regard, any of the conventional methods of blending fuels may be employed.

The following examples are illustrative of the invention, but are not intended to limit the scope of the invention or claims thereof. Unless otherwise denoted, all percentages are by weight. In the examples, "meq/g" means milliequivalents per gram.

EXAMPLE 1

Alkoxylation of Polyetheramine in a Batch Process

To a one-gallon stirring autoclave was charged 2200 grams of polyetheramine (an aminated random 4.7-mole butylene oxide and 8.8-mole propylene oxide adduct of nonylphenol with an amine value of 0.91 meq/g) and 144 grams of methanol. After purging the reactor with nitrogen, about 209 grams of 1.2-butylene oxide was introduced into the autoclave under pressure. The reactor was heated to 140 degrees Centigrade and held for about six hours. The reactor was then cooled to ambient temperature and the product was discharged. The lights were removed under reduced pressure. The resulting product was analyzed to contain 5.7 mole percent primary amine, 52.8 mole percent secondary amine and 40.2 mole percent tertiary amine. This example demonstrates ability to run at a higher reaction temperature without co-production of glycol by-product.

EXAMPLE 2

Alkoxylation of Polyetheramine in a Continuous Process

A mixture containing 867 parts of the polyetheramine used in Example 1, 62 parts of methanol and 71 parts by weight of 1,2-butylene oxide was fed into a 235 mL plug flow reactor at a rate of 120 grams per hour. The reaction was conducted at a pressure of 300 psig and 190 degrees Centigrade. The reactor effluent was stripped off to remove lights under reduced pressure and analyzed to contain 8.3 mole percent primary amine, 60.7 mole percent secondary amine and 31.0 mole percent tertiary amine.

EXAMPLE 3

Alkoxylation of Polyetheramine in a Continuous Process

The procedure of Example 2 was followed except that a mixture of 895 parts by weight of polyetheramine, 32 parts by weight of methanol and 73 parts by weight of 1,2-butylene oxide was used. The resulting product contained 15.4 mole percent primary amine, 52.7 mole percent secondary amine and 31.9 mole percent tertiary amine. As evidenced by the greater amount of unreacted primary amine-containing polyetheramine, this example indicates that relative to Example 2, less methanol relative to the polyetheramine results in a slower reaction.

EXAMPLE 4

Alkoxylation of Polyetheramine in a Continuous Process

The procedure of Example 2 was followed except that a mixture of 846 parts by weight of polyetheramine, 85 parts by weight of ethanol and 69 parts by weight of 1,2-butylene oxide was used. The resulting product contained 11.1 mole percent primary amine, 60.4 mole percent secondary amine and 28.5 mole percent tertiary amine.

What is claimed is:

1. A process for the production of an etheramine alkoxylate, comprising: reacting a polyetheramine with an alkylene oxide in the presence of an alcohol to form the etheramine alkoxylate.

2. The process of claim 1 wherein the alcohol is an aliphatic alcohol having from 1 to 12 carbon atoms.

3. The process of claim 1 wherein the alcohol is methanol, ethanol, propanol or a mixture thereof.

4. The process of claim 1 wherein the alcohol is a glycol.

5. The process of claim 1 wherein the alkylene oxide is ethylene oxide, propylene oxide, a butylene oxide or a mixture thereof.

6. The process of claim 1 wherein the polyetheramine and alkylene oxide are employed in amounts effective to form an etheramine alkoxylate of formula:

$$R-(OCH_2CHR^1)_m-N-(H)_p(CH_2CHR^3OH)_q$$

wherein R is a straight or branched alkyl, an alicyclic, an alkylalicyclic radical having from 1 to 30 carbon atoms or $R^2-Ar-$; $R^1$ and $R^3$ are each independently in each occurrence hydrogen or alkyl from 1 to 6 carbons; $R^2$ is independently in each a hydrocarbyl radical having 1 to 18 carbon atoms; m is from 2 to 20; and p+q=2.

7. The process of claim 1 wherein Ar is a divalent arylene moiety of from 6 to 24 carbon atoms.

8. The process of claim 6 wherein p is 0 or 1; and wherein q is 1 or 2.

9. The process of claim 1 wherein R is a hydrocarbyl radical of from 1 to 18 carbon atoms.

10. The process of claim 1 wherein m is from about 5 to about 20.

11. The process of claim 1 wherein the process is run batch-wise or continuously.

12. The process of claim 1 wherein the process is conducted at a temperature in the range from about 100 degrees Centigrade to about 250 degrees Centigrade.

13. The process of claim 1 wherein the polyetheramine is of formula: $R-(OCH_2CHR^1)_m-NH_2$ wherein R is a straight or branched alkyl, an alicyclic, an alkylalicyclic radical having from 1 to 30 carbon atoms or $R^2-Ar-$; $R^1$ is independently in each occurrence hydrogen or alkyl from 1 to 6 carbons; $R^2$ is independently in each a hydrocarbyl radical having 1 to 18 carbon atoms; m is from 2 to 20.

14. A process for the production of an etheramine alkoxylate, comprising: reacting a polyetheramine with an alkylene oxide in the presence of an alcohol to form the etheramine alkoxylate, wherein the alcohol is methanol, ethanol, propanol or a mixture thereof;

wherein the alkylene oxide is ethylene oxide, propylene oxide, a butylene oxide or a mixture thereof;

wherein the polyetheramine is of formula: $R-(OCH_2CHR^1)_m-NH_2$ wherein R is a straight or branched alkyl, an alicyclic, an alkylalicyclic radical having from 1 to 30 carbon atoms or $R^2-Ar-$; $R^1$ is independently in each occurrence hydrogen or alkyl from 1 to 6 carbons; $R^2$ is independently in each a hydrocarbyl radical having 1 to 18 carbon atoms; m is from 2 to 20.

15. The process of claim 14 wherein the polyetheramine and alkylene oxide are employed in amounts effective to form an etheramine alkoxylate of formula:

$$R-(OCH_2CHR^1)_m-N-(H)_p(CH_2CHR^3OH)_q$$

wherein R is a straight or branched alkyl, an alicyclic, an alkylalicyclic radical having from 1 to 30 carbon atoms or $R^2-Ar-$; $R^1$ and $R^3$ are each independently in each occurrence hydrogen or alkyl from 1 to 6 carbons; $R^2$ is independently in each a hydrocarbyl radical having 1 to 18 carbon atoms; m is from 2 to 20; and p+q=2.

16. The process of claim 15 wherein Ar is a divalent arylene moiety of from 6 to 24 carbon atoms.

17. The process of claim 16 wherein p is 0 or 1; and wherein q is 1 or 2.

18. The process of claim 17 wherein R is a hydrocarbyl radical of from 1 to 18 carbon atoms.

19. The process of claim 18 wherein m is from about 5 to about 20.

20. The process of claim 14 wherein the process is conducted at a temperature in the range from about 100 degrees Centigrade to about 250 degrees Centigrade.

* * * * *